US009458419B2

(12) United States Patent
Edgington et al.

(10) Patent No.: US 9,458,419 B2
(45) Date of Patent: Oct. 4, 2016

(54) POLYMER COMPOSITION AND METHOD FOR REMOVING CONTAMINATES FROM A SUBSTRATE

(75) Inventors: Garry Edgington, Honolulu, HI (US); Shaosheng Dong, Honolulu, HI (US); Ge Ming Lui, Honolulu, HI (US); Hank Wuh, Honolulu, HI (US); Stephen L. Sherman, Haleiwa, HI (US)

(73) Assignee: Cellular Bioengineering, Inc., Honolulu, HI (US)

( * ) Notice: Subject to any disclaimer, the term of this patent is extended or adjusted under 35 U.S.C. 154(b) by 1898 days.

(21) Appl. No.: 11/680,050

(22) Filed: Feb. 28, 2007

(65) Prior Publication Data

US 2012/0121459 A1 May 17, 2012

Related U.S. Application Data

(60) Provisional application No. 60/777,266, filed on Feb. 28, 2006.

(51) Int. Cl.
*A61L 2/00* (2006.01)
*A61L 2/18* (2006.01)
(Continued)

(52) U.S. Cl.
CPC ............. *C11D 17/041* (2013.01); *C11D 3/222* (2013.01); *C11D 3/223* (2013.01); *C11D 3/225* (2013.01);
(Continued)

(58) Field of Classification Search
CPC ............................ A61K 9/7015; A01N 37/44
USPC ............................................ 422/28; 252/397
See application file for complete search history.

(56) References Cited

U.S. PATENT DOCUMENTS 4,097,437 A 6/1978 Dhake
4,241,141 A 12/1980 Dill ................................ 428/500

(Continued)

FOREIGN PATENT DOCUMENTS

DE 26 03 290 1/1976
EP 0 916 682 5/1999

(Continued)

OTHER PUBLICATIONS

Modec Inc., Technical Report MOD2003-1012-G Issued Feb. 2003, Formulations for the Decontamination and Mitigation of CB Warfare Agents, Toxic Hazardous Materials, Viruses, Bacteria and Bacterial Spores.

(Continued)

*Primary Examiner* — Jill Warden
*Assistant Examiner* — Brittany Fisher
(74) *Attorney, Agent, or Firm* — Renner, Otto, Boisselle & Sklar, LLP

(57) ABSTRACT

This invention relates to an aqueous polymer composition and to films formed from this aqueous composition. The aqueous composition may be used in a method for removing contaminate material from a substrate. The aqueous polymer composition may comprise: water; and at least one water-soluble film forming polymer. In one embodiment, the aqueous composition may further comprise at least one chelating agent and/or at least one surfactant. The aqueous polymer composition may be applied to a contaminated substrate or to a clean substrate which is subjected to subsequent contamination. The aqueous composition may be dehydrated and/or the polymer may be crosslinked to form a film. When applied to a contaminated substrate, the film may combine with the contaminates. When applied to a clean substrate, the contaminate material may subsequently contact and adhere to the film. The film combined with the contaminate material may be separated from the substrate, with the result being removal of the contaminate material from the substrate.

5 Claims, 1 Drawing Sheet

(51) Int. Cl.

| | |
|---|---|
| ***C11D 17/04*** | (2006.01) |
| ***C11D 3/22*** | (2006.01) |
| ***C11D 3/37*** | (2006.01) |
| ***C11D 11/00*** | (2006.01) |

(52) U.S. Cl.

CPC ............... *C11D 3/226* (2013.01); *C11D 3/227* (2013.01); *C11D 3/228* (2013.01); *C11D 3/3753* (2013.01); *C11D 3/3765* (2013.01); *C11D 3/3773* (2013.01); *C11D 3/3776* (2013.01); *C11D 11/0005* (2013.01); *C11D 11/0023* (2013.01); *Y10T 428/31855* (2015.04)

(56) References Cited

U.S. PATENT DOCUMENTS

| | | | | |
|---|---|---|---|---|
| 4,482,680 | A | 11/1984 | Sheldon et al. | 525/331.4 |
| 4,598,122 | A | 7/1986 | Goldenberg | 525/61 |
| 4,748,049 | A | 5/1988 | Charles et al. | 427/156 |
| 4,978,713 | A | 12/1990 | Goldenberg | 525/61 |
| 5,091,447 | A | 2/1992 | Lomasney | 523/408 |
| 5,133,117 | A | 7/1992 | Lomasney | 29/110.5 |
| 5,143,949 | A | 9/1992 | Grogan et al. | 523/334 |
| 5,174,929 | A | 12/1992 | Janssen et al. | 264/2.6 |
| 5,376,527 | A | 12/1994 | Robson et al. | 435/6 |
| 5,387,434 | A | 2/1995 | Black | 427/154 |
| 5,405,509 | A | 4/1995 | Lomasney et al. | 204/130 |
| 5,418,006 | A | 5/1995 | Roth et al. | 427/154 |
| 5,421,897 | A | 6/1995 | Grawe | 134/6 |
| 5,454,867 | A | 10/1995 | Brothers et al. | 106/724 |
| 5,508,317 | A | 4/1996 | Muller | 522/85 |
| 5,509,969 | A | 4/1996 | Grawe | 134/2 |
| 5,631,042 | A | 5/1997 | Becker et al. | 427/154 |
| 5,681,399 | A | 10/1997 | Okano | 134/4 |
| 5,731,057 | A | 3/1998 | Montoya | 428/142 |
| 5,753,563 | A | 5/1998 | Guan et al. | 438/476 |
| 6,123,777 | A | 9/2000 | Sakurai et al. | 134/4 |
| 6,139,963 | A | 10/2000 | Fujii et al. | 428/407 |
| 6,682,773 | B2 | 1/2004 | Medwick et al. | 427/154 |
| 6,710,126 | B1 | 3/2004 | Hirt et al. | 525/61 |
| 6,855,743 | B1 | 2/2005 | Gvozdie | 521/141 |
| 6,958,372 | B2 | 10/2005 | Parker et al. | 525/61 |
| 6,960,617 | B2 | 11/2005 | Omidian et al. | 521/102 |
| 2002/0122831 | A1 | 9/2002 | Mowrey-McKee et al. | 424/616 |
| 2003/0198807 | A1* | 10/2003 | Banba | C09J 7/0246 428/343 |
| 2004/0013638 | A1 | 1/2004 | Aubay et al. | 424/78.37 |
| 2004/0096589 | A1 | 5/2004 | Eoga | 427/385.5 |
| 2005/0049181 | A1 | 3/2005 | Madhyastha | 514/8 |
| 2005/0061357 | A1 | 3/2005 | Steward et al. | |
| 2005/0079150 | A1 | 4/2005 | Gellman et al. | 424/78.27 |
| 2005/0277568 | A1 | 12/2005 | Keenan et al. | 510/438 |
| 2006/0018853 | A1 | 1/2006 | Watanabe | |
| 2007/0275101 | A1 | 11/2007 | Lu et al. | 424/719 |
| 2008/0317949 | A1 | 12/2008 | Edgington et al. | 427/154 |

FOREIGN PATENT DOCUMENTS

| | | |
|---|---|---|
| EP | 1 074 311 A1 | 2/2001 |
| JP | 60 100098 | 3/1985 |
| JP | 61 269095 | 11/1986 |
| WO | 85/05294 | 12/1985 |
| WO | 96/40454 | 12/1996 |
| WO | 01/54836 | 8/2001 |
| WO | 03/054134 | 7/2003 |
| WO | 2005/085406 | 9/2005 |
| WO | 2006/081617 | 8/2006 |
| WO | 2007/100861 | 9/2007 |

OTHER PUBLICATIONS

Initiatives Online, vol. 7, Fall 2000, "Spotlight on the D&D Focus Area.".

Archibald et al.; "Cleaning and Decontamination using Strippable and Protective Coatings at the Idaho National Engineering and Environmental Laboratory"; Lockheed Martin Idaho Technology Company (1999).

Carboline; Alara® 1146 Strippable Coating product information; Feb. 2003.

Innovative Technology Summary Report; ALARA ™ 1146 Strippable Coating; Deactivation and Decommissioning Focus Area; Prepared for U.S. Department of Energy; Apr. 2000.

Ricciardi et al.; *Chem. Mater.*, 2005, 17, 1183-1189.

Wu et al.; *Macromolecules* 1990, 23, 2245-2251.

Bonapasta et al.; *Chem. Mater.* 2002, 14, 1016-1022.

Coker; *Industrial Engineering and Chemistry*, vol. 49, No. 3, 1957.

Technology Evaluation Report; "Evaluation of Spray-Applied Sporicidal Decontamination Technologies"; United States Environmental Protection Agency, Office of Research and Development; EPA 600/R-06/146, Sep. 2006.

Kramer et al.; "How long do nosocomial pathogens persist on inanimate surfaces?"; *BMC Infectious Diseases*, 2006.

Weber et al.; "Outbreaks Associated with Contaminated Antiseptics and Disinfectants"; *Antimicrobial Agents and Chemotherapy*; vol. 51, No. 12; Dec. 2007; pp. 4217-4224.

Witney et al.; "Inactivation of *Bacillus anthracis* Spores"; *Emerging Infectious Diseases*; vol. 9, No. 6, Jun. 2003; pp. 623-627.

Drake et al.; "Side-by-Side Performance Comparison of Chemical-Based Decontamination Products for Dirty Bomb Cleanup—11099"; WM2011 Session 069.

Drake; Technology Evaluation Report; CBI Polymers DeconGel® 1101 and 1108 for Radiological Decontamination; Jun. 2011.

Co-pending U.S. Appl. No. 13/570,479, filed Aug. 9, 2012.

Co-pending U.S. Appl. No. 12/142,059, filed Jun. 19, 2008.

Co-pending U.S. Appl. No. 12/142,018, filed Jun. 19, 2008.

International Search Report and Written Opinion, Application No. PCT/US2007/005181, mailed Aug. 8, 2007.

Communication pursuant to Article 94(3) EPC, Application No. 07 751 912.2-2114, dated Mar. 3, 2009.

Communication pursuant to Article 94(3) EPC, Application No. 07 751 912.2-2114, dated Nov. 16, 2009.

* cited by examiner

POLYMER COMPOSITION AND METHOD FOR REMOVING CONTAMINATES FROM A SUBSTRATE

This application claims priority under 35 U.S.C. §119(e) to U.S. Provisional Application Ser. No. 60/777,266 filed Feb. 28, 2006. This prior application is incorporated herein by reference.

TECHNICAL FIELD

This invention relates to polymer compositions and to methods for removing contaminate materials from substrates using the foregoing polymer compositions. The polymer compositions may comprise aqueous compositions which upon dehydrating and/or crosslinking form peelable or strippable films capable of decontaminating substrates of a wide variety of contaminates including radionuclides, bacteria, viruses, fungi, chemical and biological warfare agents, toxic chemicals, as well as other contaminants. The films may be referred to as strippable or peelable hydrogels.

BACKGROUND

Improved radiological surface decontamination techniques can result in lowered dose, reduced down time, and major cost savings in the cleanup incurred in the various phases of operation and closure of nuclear facilities. Surface decontamination projects are wide-ranging in scope, magnitude, and complexity. These methods may be used to remove fixed and/or loose contamination without disturbing the surface of the substrate. Technologies that may be used include chemical, mechanical, and thermal methods such as compressed air blasting, cryogenic $CO_2$ blasting, high-pressure water, superheated water, water flushing, steam cleaning, hand brushing, automated brushing, sponge blasting, hot air stripping, dry heat, solvent washing, vacuum cleaning and ultrasonic cleaning. There are problems with each of these techniques. The present invention provides a solution to one or more of these problems.

SUMMARY

This invention relates to an aqueous polymer composition and to films formed from this aqueous composition. The films may be referred to as hydrogels. The aqueous polymer composition may be used in methods for removing contaminate materials from substrates. The aqueous polymer composition may comprise: water; and at least one water-soluble film forming polymer. In one embodiment, the aqueous polymer composition may further comprise at least one chelating agent, at least one surfactant, or a mixture thereof. In one embodiment, the aqueous polymer composition may be applied to a contaminated substrate and then the composition may be dehydrated and/or the polymer may be crosslinked to provide for the formation of a film. When applied to a contaminated substrate, the film may combine with the contaminates. The film combined with the contaminates may be separated (e.g., stripped or peeled) from the substrate, with the result being removal of the contaminates from the substrate. Alternatively, the film may be applied to a to clean substrate which is subjected to subsequent contamination wherein the contaminate material is deposited in or on the film and subsequently removed with the film.

The present invention provides advantages over techniques used in the art wherein additional waste streams may be generated that must be contained, managed and/or further processed. For example, liquids which once applied become radioactive may pose run-off and further contamination risks. Blasting or other mechanical removal techniques such as grinding, milling and scabbling, generate rubble, debris and dust that may go airborne, further posing risk to personnel and spreading contamination.

The present invention may involve "painting" a surface, for example, with the aqueous polymer composition which can reach into the nooks and crannies and encapsulate and peel away the offending contaminant offering an increased degree of efficacy, help prevent the airborne spread of the contamination, and eliminate the hazards and nuisance of further spread and waste processing of messy detergent and rinse solutions.

The present invention may be applicable to decontamination situations such as in the field of nuclear medicine where technologists in hospitals or other treatment facilities deal with radiological decontamination in the course of their work in and around medicine compounding areas, floors, medical equipment, operating tables, gurneys, heart stress test rooms, and the like. Similar situations may exist in research laboratories that utilize radioactive materials. The invention may be applicable to decontamination situations involving radionuclides, bacteria, viruses, fungi, chemical and biological warfare agents, toxic chemicals, as well as other contaminants, and the like.

In one embodiment, the invention relates to a composition, comprising: water; at least one water-soluble film forming polymer; at least one chelating agent; and at least one surfactant.

In one embodiment, the invention relates to a composition made by combining at least one water-soluble film forming polymer, and at least one chelating agent, and at least one surfactant.

In one embodiment, the invention relates to a method for removing contaminate material from a substrate, comprising: applying an aqueous composition comprising at least one water soluble film-forming polymer to the substrate in contact with the contaminate material; dehydrating the aqueous composition and/or crosslinking the polymer to form a film, the contaminate material combining with the film; and separating the film from the substrate.

In one embodiment, the invention relates to a method for removing contaminate material from a substrate, comprising: applying an aqueous composition comprising at least one water soluble film-forming polymer to the substrate; dehydrating the aqueous composition and/or crosslinking the polymer to form a film; depositing a contaminate material in or on the film; and separating the film from the substrate.

In one embodiment, the invention relates to a laminate, comprising: a release liner; and a film layer derived from the foregoing aqueous composition overlying part or all of one side of the release liner.

In one embodiment, the invention relates to a laminate, comprising: a film layer derived from the foregoing aqueous composition, the film layer having a first side and a second side; a first release liner overlying the first side of the film layer; and a second release liner overlying the second side of the film layer.

In one embodiment, the inventive method may be used to provide for a fixative wherein the contaminate material is immobilized and disposal is carried out at a later time. Alternatively, disposal may be carried out immediately.

DETAILED DESCRIPTION

The term "water-soluble" may be used to refer to a material that is soluble in water at a temperature of 20° C. to the extent of at least about 5 grams of the material per liter of water. The term "water-soluble" may also refer to a material that forms an emulsion in water.

The term "water-soluble film forming polymer" may refer to a polymer which may be dissolved in water and upon evaporation of the water form a film or coating layer.

The term "biodegradable" may refer to a material that degrades to form water and $CO_2$.

Figure 1:
FIGS. 1-3 are photographs showing the application of the aqueous polymer composition to a substrate, and after evaporation of water from the aqueous polymer composition removal of the resulting film from the substrate.
Figure 2:
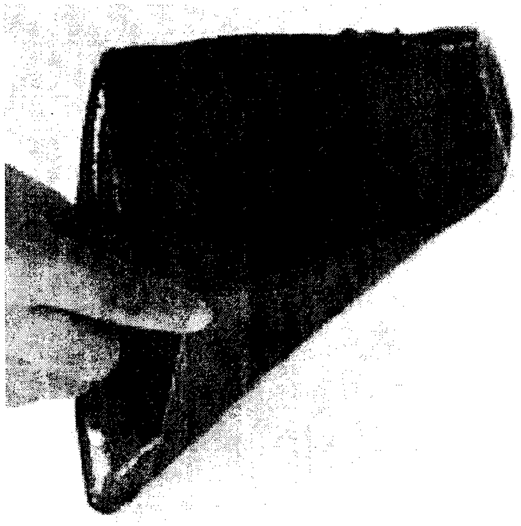
Figure 3:
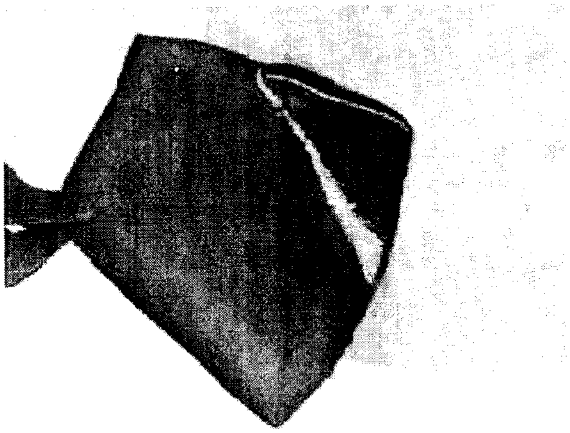

The aqueous polymer composition may comprise water, and at least one water-soluble film forming polymer. In one embodiment, the aqueous composition may further comprise at least one chelating agent, at least one surfactant, or a mixture thereof. The aqueous polymer composition may be applied to a substrate using conventional coating techniques, for example, brushing, rolling, spraying, spreading, dipping, smearing, and the like. In one embodiment, the aqueous polymer composition may comprise a two component reactive coating composition where the two components are mixed before application, mixed at the time of application (e.g., during spraying), or applied as separate coats. The substrate may comprise a contaminated substrate wherein the film is applied to the contaminated substrate and the contaminate material is taken up by the film. Alternatively, the film may be applied to a clean substrate which is subjected to subsequent contamination wherein the contaminate material is deposited on or in the film and subsequently removed with the film. After application of the aqueous polymer composition to the substrate, the aqueous composition may be dehydrated and/or the polymer may be crosslinked to provide the film. Dehydration may be enhanced using fans, dehumidifiers, a heat source, or a combination thereof. The contaminate material may be taken up, sorbed and/or complexed by or with the polymer composition or components of the polymer composition. The contaminate material may be on the surface of the film. The film combined with the contaminate material may be separated from the substrate leaving a non-contaminated surface or a surface with a reduced level of contamination. For example, the film may be stripped or peeled from the substrate. This is shown in FIGS. 1-3. The polymer composition may be used to remove dirt, biological agents, chemical agents, heavy metals, radioactive materials, and the like, from substrates such as human skin, wounds in human skin, porous and non porous substrates, and the like. The water-soluble film forming polymer may comprise a hydrophobic backbone and hydrophilic hydroxyl groups. The polymer may comprise a block copolymer with one or more hydrophobic blocks and one or more hydrophilic blocks. The polymer may comprise vinyl alcohol repeating units. The polymer may comprise polyvinyl alcohol, a copolymer of vinyl alcohol, or a mixture thereof. The term "copolymer" may be used herein to refer to a polymer with two or more different repeating units including copolymers, terpolymers, and the like. The polymer may comprise one or more polysaccharides. The polymer may comprise a mixture of one or more vinyl alcohol polymers and/or copolymers and one or more polysaccharides. The polymer may be biodegradable. The polymer may be a crosslinkable polymer, and crosslinking agents may be included in the polymer composition to enhance crosslinking.

The polymer may comprise an atactic polyvinyl alcohol. These polymers may have a semicrystalline character and a strong tendency to exhibit both inter-molecular and intra-molecular hydrogen bonds.

The polymer may comprise repeating units represented by the formula $—CH_2—CH(OH)—$ and repeating units represented by the formula —CH2—CH(OCOR)— wherein R is an alkyl group. The alkyl group may contain from 1 to about 6 carbon atoms, and in one embodiment from 1 to about 2 carbon atoms. The number of repeating units represented by the formula $—CH_2—CH(OCOR)—$ may be in the range from about 0.5% to about 25% of the repeating units in the polymer, and in one embodiment from about 2 to about 15% of the repeating units. The ester groups may be substituted by acetaldehyde or butyraldehyde acetals.

The polymer may comprise a poly(vinyl alcohol/vinyl acetate) structure. The polymer may be in the form of a vinyl alcohol copolymer which also contains hydroxyl groups in the form of 1,2-glycols, such as copolymer units derived from 1,2-dihydroxyethylene. The copolymer may contain up to about 20 mole % of such units, and in one embodiment up to about 10 mole % of such units.

The polymer may comprise a copolymer containing vinyl alcohol and/or vinyl acetate repeating units and repeating units derived from one or more of ethylene, propylene, acrylic acid, methacrylic acid, acrylamide, methacrylamide, dimethacrylamide, hydroxyethylmethacrylate, methyl methacrylate, methyl acrylate, ethyl acrylate, vinyl pyrrolidone, hydroxyethylacrylate, allyl alcohol, and the like. The copolymer may contain up to about 50 mole % of repeating units other than those of to vinyl alcohol or vinyl acetate, and in one embodiment from about 1 to about 20 mole % of such repeating units other than vinyl alcohol or vinyl acetate.

Polyvinyl alcohols that may be used may include those available under the tradenames Celvol 523 from Celanese (MW=85,000 to 124,000, 87-89% hydrolyzed), Celvol 508 from Celanese (MW=50,000 to 85,000, 87-89% hydrolyzed), Celvol 325 from Celanese (MW=85,000 to 130,000, 98-98.8% hydrolyzed), Vinol® 107 from Air Products (MW=22,000 to 31,000, 98-98.8% hydrolyzed), Polysciences 4397 (MW=25,000, 98.5% hydrolyzed), BF 14 from Chan Chun, Elvanol® 90-50 from DuPont and UF-120 from Unitika. Other producers of polymers that may be used may include Nippon Gohsei (Gohsenol®), Monsanto (Gelvatol®), Wacker (Polyviol®) or the Japanese producers Kuraray, Deriki, and Shin-Etsu.

The polymer may comprise vinyl acetate, hydrolyzed or partially hydrolyzed vinyl acetate, and additional comonomers. These may be obtainable, for example, as hydrolyzed ethylene-vinyl acetate (EVA), vinyl chloride-vinyl acetate, N-vinylpyrrolidone-vinyl acetate, or maleic anhydride-vinyl acetate. If the polymer is a copolymer of vinyl acetate and N-vinylpyrrolidone, the polymers available under the name Luviskol® from BASF may be used. These may include Luviskol VA 37 HM, Luviskol VA 37 E and Luviskol VA 28.

The polymer may comprise one or more water-soluble polysaccharides. These may include carboxymethylcelluloses, cellulose acetates, cellulose acetate butyrates, cellulose nitrates, ethylcelluloses, hydroxyalkylcelluloses (e.g., hyd roxymethylcellu lose), hydroxyalkylalkylcelluloses, methylcelluloses, starch, starch acetates, starch 1-octenylsuccinates, starch phosphates, starch succinates, hydroxyethylstarches, hydroxypropylstarches, cationic starches, oxidized starches, dextrins, or a mixture of two or more thereof.

The polymer may have a weight average molecular weight of at least about 10,000 g/mol. The polymer may have a weight average molecular weight of up to about 1,000,000 g/mol. The polymer may have a weight average molecular weight in the range from about 10,000 to about 1,000,000 g/mol, and in one embodiment from about 13,000 g/mol to about 250,000 g/mol, and in one embodiment from about 13,000 g/mol to about 186,000 g/mol.

The polymer may have a hydrolysis level in the range from about 75% to about 100%, and in one embodiment from about 86% to about 99.3%.

The concentration of the water-soluble film forming polymer in the aqueous polymer composition may be in the range from about 1 to about 60% by weight, and in one embodiment from about 5 to about 40% by weight.

The aqueous polymer composition may have a concentration of water in the range from about 40 to about 99% by weight, and in one embodiment from about 60 to about 95% by weight. The water may be derived from any source. The water may comprise deionized or distilled water. The water may comprise tap water.

The chelating agent, or chelant, may comprise one or more organic or inorganic compounds that contain two or more electron donor atoms that form coordinate bonds to metal ions or other charged particles. After the first such coordinate bond, each successive donor atom that binds may create a ring containing the metal or charged particle. The structural aspects of a chelate may comprise coordinate bonds between a metal or charged particle, which may serve as an electron acceptor, and two or more atoms in the molecule of the chelating agent, or ligand, which may serve as the electron donors. The chelating agent may be bidentate, tridentate, tetradentate, pentadentate, and the like, according to whether it contains two, three, four, five or more donor atoms capable of simultaneously complexing with the metal ion or charged particle.

The chelating agent may comprise an organic compound that contains a hydrocarbon linkage and two or more functional groups. The same or different functional groups may be used in a single chelating agent. The functional groups may include ═X, —XR, —$NR_2$, —$NO_2$═NR, ═NXR, ═N—R*—XR,

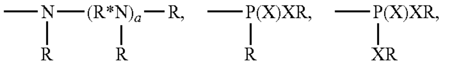

wherein X is O or S, R is H or alkyl; R* is alkylene, and a is a number ranging from zero to about 10.

Examples of chelating agents that may be used may include ethylenediaminetetraacetic acid (EDTA), diethylenetriaminepentaacetic acid (DTPA), Prussian Blue, citric acid, peptides, amino acids including short chain amino acids, aminopolycarboxylic acids, gluconic acid, glucoheptonic acid, organophosphonates, bisphosphonates such as pamidronate, inorganic polyphosphates, and the like. Salts of the foregoing chelating agents may be used. These may include sodium, calcium and/or zinc salts of the foregoing. The sodium, calcium and/or zinc salts of DTPA, especially sodium salts of DTPA, may be used. Salts of the foregoing chelating agents may be formed when neutralizing with, for example, sodium hydroxide.

The concentration of the chelating agent in the aqueous polymer composition may be in the range from about 0.1 to about 5% by weight, and in one embodiment from about 0.5 to about 2% by weight.

The surfactant may comprise one or more ionic and/or nonionic compounds having a hydrophilic lipophilic balance (HLB) in the range of zero to about 18 in Griffin's system, and in one embodiment from about 0.01 to about 18. The ionic compounds may be cationic or amphoteric compounds. Examples may include those disclosed in *McCutcheons Surfactants and Detergents,* 1998, North American & International Edition. Pages 1-235 of the North American Edition and pages 1-199 of the International Edition are incorporated herein by reference for their disclosure of such surfactants. The surfactants that may be used may include alkanolamines, alkylarylsulfonates, amine oxides, poly(oxyalkylene) compounds, including block copolymers comprising alkylene oxide repeat units, carboxylated alcohol ethoxylates, ethoxylated alcohols, ethoxylated alkyl phenols, ethoxylated amines and amides, ethoxylated fatty acids, ethoxylated fatty esters and oils, fatty esters, fatty acid amides, glycerol esters, glycol esters, sorbitan esters, imidazoline derivatives, lecithin and derivatives, lignin and derivatives, monoglycerides and derivatives, olefin sulfonates, phosphate esters and derivatives, propoxylated and ethoxylated fatty acids or alcohols or alkyl phenols, sorbitan derivatives, sucrose esters and derivatives, sulfates or alcohols or ethoxylated alcohols or fatty esters, sulfonates of dodecyl and tridecyl benzenes or condensed naphthalenes or petroleum, sulfosuccinates and derivatives, and tridecyl and dodecyl benzene sulfonic acids. The surfactant may comprise sodium lauryl sulfonate, cetyltrimethyl ammonium bromide, and the like.

The concentration of the surfactant in the aqueous polymer composition may be in the range up to about 10% by weight of the composition, and in one embodiment in the range from about 0.1 to about 5% by weight, and in one embodiment from about 0.5 to about 2% by weight, and in one embodiment in the range from about 1 to about 2% by weight.

The polymer composition may further comprise one or more thixotropic additives, pseudoplastic additives, rheology modifiers, anti-settling agents, leveling agents, defoamers, pigments, dyes, organic solvents, plasticizers, viscosity stabilizers, biocides, viricides, fungicides, chemical warfare agent neutralizers, crosslinkers, humectants, neutron absorbers, or a mixture of two or more thereof. The thixotropic additive may comprise fumed silica, treated fumed silica, clay, hectorite clay, organically modified hectorite clay, thixotropic polymers, pseudoplastic polymers, polyurethane, polyhydroxycarboxylic acid amides, modified urea, urea modified polyurethane, or a mixture of two or more thereof. The leveling agent may comprise polysiloxane, dimethylpolysiloxane, polyether modified dimethylpolysiloxane, polyester modified dimethylpolysiloxane, polymethylalkysiloxane, aralkyl modified polymethylalkylsiloxane, alcohol alkoxylates, polyacrylates, polymeric fluorosurfactants, fluoro modified polyacrylates, or a mixture of two or more thereof. The organic solvent may comprise one or more alcohols, for example, methanol, ethanol, propanol, butanol, one or more ketones, for example, acetone, one or more acetates, for example, methyl acetate, or a mixture of two or more thereof. The plasticizer may comprise ethylene glycol, polyethylene glycol, propylene glycol, polypropylene glycol, butane diol, polybutylene glycol, glycerine, or a mixture of two or more thereof. The viscosity stabilizer may comprise a mono or multifunctional hydroxyl compound. These may include methanol, ethanol, propanol, butanol, ethylene glycol, polyethylene glycol, propylene glycol, polyethylene glycol, propylene glycol, polypropylene glycol, butane diol, polybutylene glycol, glycerine, or a mixture of two or more thereof. The biocide may comprise Kathon LX (a product of Rohm and Hass Company comprising 5-chloro-2-methyl-4-isothiazolin-3-one and 2-methyl-4-isothiazolin-3-one) or Dowacil 75 (a product of Dow Chemical comprising 1-(3-chloroallyl)-3,5,7-triaza-1-azoniaadamantane chloride). The crosslinker may comprise sodium tertraborate, glyoxal, Sunrez 700 (a product of Sequa Chemicals identified as cyclic urea/glyoxal/polyol condensate), Bacote-20 (a product of Hopton Technology identified as stabilized ammonium zirconium carbonate), polycup-172 (a product of Hercules, Inc. identified as a polyamide-epichlorohydrin resin), ora mixture of two or more thereof. The neutron absorber may be used to reduce criticality risk during the decontamination of fissile materials. The neutron absorber may comprise a compound which may comprise a boron atom such as sodium tetraborate. The biocide, viricide or fungicide may have the capability of killing common biological warfare agents and other resistant biological contaminates. The biocide, viricide or fungicide may comprise sodium hypochlorite, potassium hypochlorite, pH-amended sodium hypochlorite, quaternary ammonium chloride, pH-amended bleach (Clorox®), CASCAD™ surface decontamination foam (AllenVanguard), DeconGreen (Edgewood Chemical Biological Center), DioxiGuard (Frontier Pharmaceutical), EasyDecon 200 (Envirofoam Technologies), Exterm-6 (ClorDiSys Solutions), HI-Clean 605 (Howard Industries), HM-4100 (Biosafe) KlearWater (Disinfection Technology), Peridox (Clean Earth Technologies) Selectrocide (BioProcess Associates), EasyDECON™ 200 decontamination solution or a mixture of two or more thereof. Chemical warfare agent neutralizers may comprise potassium permanganate, potassium peroxydisulfate, potassium peroxymonosulfate (Virkon S®), potassium molybdate, hydrogen peroxide, chloroisocyanuric acid salt, sodium hypochlorite, potassium hypochlorite, pH-amended sodium hypochlorite, hydrogen peroxide, oxidants, nucleophiles, hydroxide ions, catalytic enzymes, organophosphorous acid anhydrolase, o-iodosobenzoate, iodoxybenzoate, perborate, peracetic acid, m-chloroperoxybenzoic acid, magnesium monoperoxyphthalate, benzoyl peroxide, hydroperoxy carbonate ions, polyoxymetalates, quaternary ammonium complexes, Sandia Foam (Sandia National Laboratories), EasyDECON™ 200 Decontamination Solution, Modec's Decon Formula (Modec, Inc.) or a mixture of two or more thereof. The humectant may comprise polyacrylic acid, polyacrylic acid salt, an acrylic acid copolymer, a polyacrylic acid salt copolymer, or a mixture of two or more thereof. The concentration of each of these in the aqueous polymer composition may be up to about 25% by weight, and in one embodiment up to about 10% by weight.

The aqueous polymer composition may have a broad range of viscosities and rheological properties which allows the aqueous polymer composition to diffuse into the substrate (i.e., clean or contaminated substrate) for a relatively deep cleaning, allow for a variety of application methods including application via brush, roller or spray equipment, and to allow for a thick enough wet film on non-horizontal surfaces to result in a dry film with sufficient strength to allow for removal by peeling or stripping the film. The surfactant may be used to control or enhance these rheological properties. The Brookfield Viscosity of the aqueous polymer composition may be in the range from about 100 to about 500,000 centipoise, and in one embodiment in the range from about 200 to about 200,000 centipoise measured at the rpm and spindle appropriate for the sample in the range of 0.3-60 rpm and spindles 1-4 at 25° C.

When the polymer composition is dehydrated and/or the polymer is crosslinked, the resulting film composition may encapsulate, entrap, solublize or emulsify both hydrophobic and hydrophilic material as well as neutralize both chemical and biological toxins. The chelating agent may be used to form complexes with contaminate materials such as metal ions and other charged particles (e.g., heavy metals, radioactive materials, and the like) wherein the resulting complex may be removed from the substrate with the polymer composition. The film may have a concentration of water in the range from about 30 to about 97% by weight, and in one embodiment from about 50 to about 95% by weight. As indicated above, this film may be referred to as a hydrogel, and in one embodiment a strippable or peelable hydrogel. The film may have a thickness and tensile strength sufficient to allow for it to be stripped or peeled from the substrate. The film thickness may be in the range from about 0.25 to about 50 mils, and in one embodiment from about 0.5 to about 10 mils. Upon separating (e.g., stripping or peeling) the film from the substrate, the contaminate material may be taken up with the film and thereby removed from the substrate.

In one embodiment, the polymer composition may be applied to the substrate using a laminate structure. The laminate structure may comprise a layer of the film overlying part or all of one side of a release liner. Alternatively, the film layer may be positioned between two release liners. The film layer may be formed by coating one side of the release liner with the aqueous polymer composition using conventional techniques (e.g., brushing, roller coating, spraying, and the like) and then dehydrating the aqueous composition and/or crosslinking the polymer to form the film layer. If the laminate structure comprises a second release liner, the second release liner may then be placed over the film layer on the side opposite the first to release liner. The film layer may have a thickness in the range from about 1 to about 500 mils, and in one embodiment from about 5 to about 100 mils. The release liner(s) may comprise a backing liner with a release coating layer applied to the backing liner. The release coating layer contacts the film layer and is provided to facilitate removal of the release liner from the film layer. The backing liner may be made of paper, cloth, polymer film, or a combination thereof. The release coating may comprise any release coating known in the art. These may include silicone release coatings such as polyorganosiloxanes including polydimethylsiloxanes. When the laminate structure comprises a release liner on one side of the film layer, the laminate structure may be provided in roll form. The film layer may be applied to a substrate by contacting the substrate with the film layer, and then removing the release liner from the film layer. The film layer may be sufficiently tacky to adhere to the substrate. When the laminate structure comprises a release liner on both sides of the film layer, the laminate structure may be provided in the form of flat sheets. The film layer may be applied to a substrate by peeling off one of the release liners from the laminate structure, contacting the substrate with the film layer, positioning the film layer on the substrate, and then removing the other release liner from the film layer.

The substrates that may be treated with the inventive polymer compositions may include human skin and wounds, as well as wood, metal, glass, concrete, painted surfaces, plastic surfaces, and the like. The substrate may comprise a porous or non-porous material. The substrate may comprise horizontally aligned non-porous substrates such as floors, counter tops, table tops, medical equipment, gurneys, heart stress test room surfaces, toilet seats, as well as complex three dimensional structures such as faucets, tools and other types of equipment or infrastructure and the like. The inventive polymer compositions may be used to decontaminate buildings, medical facilities and articles of manufacture, buildings and infrastructure intended for demolition, military assets, airplanes, as well as ship interiors and exteriors of military or civilian ships.

The inventive polymer composition may be used to remove radioactive contaminants that may be found in or on the exterior of submarines and aircraft carriers as a result of activities relating to the use of nuclear materials for propulsion and weaponry. The inventive polymer compositions may be used to decontaminate to areas contaminated by spills of toxic chemicals such as wastes containing lead, cadmium, zinc, mercury, arsenic, and the like. The inventive polymer composition may be used to decontaminate areas contaminated with chemical warfare agents such as nerve agents (e.g., Tabun (ethyl-N,N-dimethyl phosphoramicocyanidate), Sarin (isopropyl methyl phosphorofluoridate), Soman (1-methyl-2:2-dimethyl propyl methyl phosphorofluoridate), and VX (ethyl S-2-diisopropylaminoethylmethyl phosphorothiolate)), and blistering agents (e.g., phosgene, mustard, and the like), as well as carcinogens, general poisons, and the like. The inventive polymer compositions may be used to decontaminate biological laboratories and military/government biological warfare research facilities from contamination ranging from the mundane, such as common bacterial and fungal contamination, to the extremely hazardous, such as anthrax, HIV and Ebola viruses. The inventive polymer composition may be used to remove hazardous waste materials from contaminated substrates. The inventive polymer composition may be used to decontaminate substrates containing radionuclides used in nuclear medicine. The inventive polymer can be used as a countermeasure to terrorist attacks to decontaminate urban infrastructure, military assets, etc. after the detonation of a radiological dispersal device (RDD) or similar device containing chemical or biological toxins or warfare agents. The inventive polymer composition may be used to decontaminate radioactive material in current and previous manufacturing settings for radiological, chemical and biological weaponry or other products.

The inventive polymer composition may comprise a rapidly deployable and low-cost chemical biological radionuclide (CBRN) decontamination product requiring minimal training for application and removal. The polymer composition may be easily contained for disposal and as a result provide rapidly restored access to operations and minimize attack/incident effects on hard assets and infrastructure. The polymer composition may be used to penetrate 'nooks and crannies', encapsulate contaminants and dry to form a tough film, allowing for peel-off removal of radioactive contamination, chemical and biological agents, hydrophilic and hydrophobic compounds as well as undesirable particulate matter. The inventive polymer composition may be used to prevent airborne spread of contaminants, and eliminate or reduce the hazards and difficulty of controlling further spread of contamination and reduce or eliminate the need for conventional waste processing such as required with the use of detergent/bleach and rinse solutions. The inventive polymer composition may be used to decontaminate the interior and exterior of military assets, buildings and structural surfaces, manufacturing facilities, power plants, shipping and transportation hubs and related transit infrastructure, and the like.

The peelability or strippability of the film may be determined subjectively. The peelability or strippability from substrates such as tile, Formica, porcelain, chrome, stainless steel, glass, sealed grout, unsealed grout, rubber, leather, plastic, painted surfaces, concrete, wood, reactors, storage vessels, and the like, may be very good.

Example 1

Fifteen (15) grams of polyvinyl alcohol (PVA) having a molecular weight of 98,000 (supplied by Sigma Aldrich) and 85 ml of water are added to a 250 ml beaker with stirring. The beaker is heated in a silicone oil bath having a temperature of 96° C. for two hours. The PVA dissolves in the water. The mixture is then cooled to room temperature. 10 ml of sodium dodecyl sulfate solution (10% by weight in water) and 5 grams of diethylenetriaminepentaacetic acid (DTPA) are added to the mixture with stirring to provide the desired aqueous polymer composition. 100 ml of the polymer composition are applied to a surface area of 370 $inches^2$ (2387 $cm^2$) using a brush to provide a uniform coating. The coating is left on the substrate for 12 hours at a temperature of 20° C. Water evaporates from the polymer composition. The resulting film is peeled off and is suitable for disposal.

Example 2

Ten (10) grams of the PVA identified in Example 1 and 75 ml of water are added to a 250 ml beaker with stirring. The beaker is heated for two hours in a silicone oil bath which is at a temperature of 96° C. The PVA dissolves in the water. The mixture is then cooled to room temperature. 10 ml of sodium dodecyl sulfate solution (10% by weight in water), 5 grams of DTPA, and 10 ml of potassium peroxymonosulfate solution (10% by weight in water) are added to the mixture with stirring to provide the desired aqueous polymer composition. 100 ml of the aqueous polymer composition are applied to a substrate having an area of 370 $inches^2$ (2387 $cm^2$) using a pump sprayer. The aqueous polymer composition is applied using two-three coats and allowed to dry for one-two hours between coats. The resulting coating is left on the substrate for 12 hours at a temperature of 20° C. Water evaporates from the polymer composition. The resulting film is peeled off and is suitable for disposal.

Example 3

Ten (10) grams of the PVA identified in Example 1 and 75 ml of water are added to a 250 ml beaker with stirring. The beaker is placed in a silicone oil bath for two hours. The silicone oil bath is at a temperature of 96° C. The PVA dissolves in the water. The mixture is then cooled to room temperature. 10 ml of sodium dodecyl sulfate solution (10% by weight in water), 5 grams of DTPA, and 10 ml of sodium hypochlorite solution (5% by weight in water) are added to the mixture with stirring to provide the desired aqueous polymer composition. The aqueous polymer is applied to a substrate using a pump sprayer. The resulting coating is applied using two-three coats and allowed to dry for one-two hours between coats. The coating is left on the substrate for 12 hours at 20° C. Water evaporates from the polymer composition. The resulting film is peeled off and is suitable for disposal.

Example 4

Ten (10) grams of the PVA identified in Example 1 and 75 ml of water are added to a 250 ml beaker. The resulting mixture is stirred and the beaker is placed in a silicone oil bath for two hours. The silicone oil bath is at a temperature of 96° C. The PVA dissolves in the water. The mixture is cooled to room temperature. 10 ml of a solution of sodium dodecyl sulfate (10% by weight in water), 5 grams of DTPA, and 10 ml of a solution of potassium peroxymonosulfate (10% by weight in water) are added to the mixture with stirring to provide the desired aqueous polymer composition. The aqueous polymer composition is applied to a substrate using a pump sprayer. The coating is applied using two-three coats. The coating is dried for one-two hours between coats. The resulting coating is left on the substrate for 12 hours at a temperature of 20° C. Water evaporates from the polymer composition. The resulting film is peeled off and is suitable for disposal.

Example 5

The aqueous polymer composition disclosed in Example 1 is applied to the sides of a phonograph record using a hand pump sprayer or a fine wide brush. The resulting coating is dried for four hours to one day resulting in the formation of a film. The film is peeled off the record to clean the grooves in the record.

Example 6

A jacketed three-liter reactor equipped with a thermocouple, condenser and stir motor is charged with 2200 g of distilled water, 45.90 g of DTPA, 6.89 g sodium dodecyl sulfate (SDS) and 65.6 g 10 N sodium hydroxide. The resulting aqueous polymer composition is agitated until the salts dissolve. This is followed by the addition of 344.4 g of Celvol 325 (a product of Celanese identified as polyvinyl alcohol, MW=85,000 to 130,000 g/mol, 98-98.8% hydrolyzed). The mixture is heated to 90° C. and held at 90° C. for 30 minutes, then cooled to yield Formulation A. Formulation A has a Brookfield Viscosity of 5100 centipoise (cps) (3 rpm, spindle 3, 25° C.) and 5480 cps (30 rpm, spindle 3, 25° C.), and pH=6.39.

Formulation A is applied to steel, aluminum, slate, glass, concrete and kitchen tile horizontal substrates using a paint brush or paint roller. The resulting films are dried overnight and then peeled off of each substrate. A thin layer of the substrate is removed when the film is peeled off of concrete. The film is peeled off of a kitchen tile that has colored blue and red chalk ground into its surface. The colored chalk is used to simulate particulate contamination. After the film is peeled from the tile substrate there is no visible chalk on the tile. The chalk side of the peeled film is then rubbed with a white paper towel with no transfer of colored chalk to the towel showing excellent encapsulation of the chalk in the peeled film.

Formulation A is tested on depleted uranium contamination in field tests to determine the decontamination factor (DF) for the material on multiple surfaces. An Eberline E600 meter is used with a 100 $cm^2$ SHP 380 alpha scintillation probe in alpha scaler mode for these tests. One minute static counts are used. The probe is positioned and a “Sharpie” (permanent marker) is used to draw around the outside of the probe to provide a reproducible geometry for subsequent measurements. Masking tape is positioned along the Sharpie lines to define the area to be tested. Formulation A is applied over the entire area with a one-inch foam brush, and overlapped on the masking tape to make the resulting film easier to remove. The floor of an area used for machining depleted uranium is decontaminated first by using tape removal then by using Formulation A. The bare floor initially has a contamination level of 9,420 cpm/100 $cm^2$. After one tape press removal it is 8,500 cpm/100 $cm^2$. After a second tape press removal it is 8,800 cpm/100 $cm^2$. After decontamination with Formulation A the activity is 357cpm/100 $cm^2$ for a DF of 24.6 or 96%.

A joint in the concrete is tested where the joint material is the typical felt used in cold joints. Formulation A is applied into the joint as part of the 100 $cm^2$ area covered. The initial activity is 24,400 cpm/100 $cm^2$. The post decontamination level is 480 cpm/100 $cm^2$ for a DF of 49.9 or 98%.

Additional tests on various substrates are summarized below.

| Material | Initial Activity* | Final Activity* | Decon Factor | Decon % |
|---|---|---|---|---|
| Floor | 1,956 | 1,345 | 1.5 | 31% |
| Stair tread | 5,470 | 3,440 | 1.6 | 37% |
| Stair tread | 5,570 | 3,690 | 1.5 | 34% |
| Rough wood | 192 | 39 | 6.0 | 80% |
| Planed wood | 168 | 36 | 4.7 | 79% |
| Oxidized steel | 2,640 | 742 | 3.6 | 72% |
| Floor | 8,800 | 357 | 24.6 | 96% |
| Floor joint | 24,400 | 480 | 49.9 | 98% |
| Plexiglas | 57 | 24 | 2.4 | 58% |
| Textured concrete block | 180 | 63 | 2.9 | 65% |

*counts/minute/100 $cm^2$ (cpm/100 $cm^2$)

Example 7

To Formulation A is added 0.072 wt % blue food coloring (a product of McCormick and Company, Inc.) to yield Formulation B. Blue food coloring is added to improve the visualization of the wet film thickness during application. Formulation B is tested in a hospital setting to remove Iodine-131 (I-131) contamination used in cancer treatments. This formulation is used to decontaminate various areas that are previously decontaminated with Radiacwash™ but still have unacceptable levels of contamination. Radiacwash™ is a standard detergent used to decontaminate radionuclides used in nuclear medicine. The removable contamination is measured before and after decontamination using Formulation B. The results are presented in the following table.

| | Initial Activity* | Final Activity* | Decon Factor | Decon % |
|---|---|---|---|---|
| Floor Tile (A) | 2000 | <600 | 3.3 | 70 |
| Floor Tile (B) | 1600 | <200 | 8.0 | 88 |
| Sink | 1000 | <50 | 20 | 95 |
| Toilet | 140,000 | 1,500 | 93 | 99 |

*disintegrations/minute (dpm)

Example 8

A jacketed three-liter reactor equipped with a thermocouple, condenser and stir motor is charged with 2295.0 g of distilled water, 27.0 g of DTPA, 27.0 g sodium dodecyl sulfate, 27.6 g of 10 N sodium hydroxide, 4.05 g of Byk-028 (product of BYK Chemie identified as hydrophobic solids and polysiloxanes). The resulting aqueous composition is agitated until the salts are dissolved followed by the addition of 405.0 g of Celvol 523. The mixture is heated to 85° C. and held at 85° C. for 30 minutes, then cooled. The pH of the mixture is adjusted with the addition of 8.8 g of 1 N NaOH to yield an aqueous polymer composition having a pH=5.5. 13.5 g of BYK-345 (a product of BYK Chemie identified as polyethermodified dimethylpolysiloxane) and 13.5 g of blue food coloring is added, followed by the drop-wise addition of 20.3 g of BYK-420 (a product of BYK Chemie identified as a modified urethane) and 20.3 g of BYK-425 (a product of BYK Chemie identified as a urea modified polyurethane). The formulation is dispersed for 15 minutes in aliquots of 200-250 ml on setting 1 of a Hamilton Beach HMD200 Mixer. 224.0 g of distilled water are then added to 2876.6 g of the combined aliquots to yield Formulation C.

Ergonomic testing was performed using Formulation C in a plutonium finishing plant for decontamination of fissile material processing areas. This testing focuses on application and removal properties in a non-contaminated stainless steel glove box used for handling fissile materials. Surfaces tested included horizontal and vertical stainless, rusted and non-rusted carbon steel, Lexan, leather and Hypalon rubber gloves. The application and removal of Formulation C is both practical and functional on both horizontal and vertical surfaces. The dried film expands after being crumpled into a ball, reducing criticality concerns when decontaminating surfaces highly contaminated with fissile materials.

Example 9

A jacketed six-liter reactor equipped with a thermocouple, condenser and stir motor is charged with 5100 g of distilled water, 60.0 g of DTPA, 60.0 g sodium dodecyl sulfate, 65.8 g of 10 N sodium hydroxide, 30 g of Byk-028 (a product of BYK Chemie identified as hydrophobic solids and polysiloxanes), and 30 g of Byk-080A (a product of BYK Chemie identified as polysiloxane copolymer). The resulting aqueous composition is agitated until the salts are dissolved followed by the addition of 900.0 g of Celvol 523. The mixture is heated to 85° C. and held at 85° C. for 30 minutes, then cooled to yield Formulation D. Formulation D has a Brookfield Viscosity of 8560 cps (1 rpm, spindle 3, 25° C.) and 10,580 cps (10 rpm, spindle 3, 25° C.). The pH is 5.74.

Example 10

A three-liter container is charged with 2539.7 of Formulation D. The formulation is agitated using a Melton CM-100 disperser equipped with 1.5 inch Cowels Blade operated at a rate of 1000-3000 rpm. 12.60 g of BYK-348 (a product of BYK Chemie identified as polyethermodified dimethylpolysiloxane) are added, followed by the drop-wise addition of 19.0 g of BYK-420 over a period of approximately 10 minutes. The rotation of the Cowles Blade is increased during addition to maintain a vortex. After the addition is complete, the formulation is dispersed for 45 minutes at 3000 rpm followed by the drop-wise addition of 19.0 g of BYK-425. The formulation is then dispersed for 15 minutes at 3000 rpm followed by the addition and 203.2 g of distilled water. The formulation is dispersed for an additional 15 minutes at 3000 rpm. To 2039.6 g of the resulting formulation are added 5.4 g blue food coloring to yield Formulation E. Formulation E has a Brookfield Viscosity of 19,960 cps (3 rpm, spindle 4, 25° C.) and 15,790 cps (30 rpm, spindle 4, 25° C.).

A film formed using Formulation E is peeled off of a kitchen tile with a semi-porous surface which is colored with blue and red chalk. The chalk is ground into to the semi-porous surface. The colored chalk is chosen to simulate particulate contamination. After the film is peeled from the substrate there is no visible chalk on the tile. The chalk side of the peeled film is rubbed with a white paper towel with no transfer of colored chalk to the towel showing excellent encapsulation of the chalk.

Formulation E is evaluated in a hospital setting to remove Iodine-131 (I-131) contamination used in cancer treatments. The removable contamination on the surface of various substrates is measured before and after decontamination with Formulation E with results showing excellent decontamination. Additionally, the removable contamination on the top surface and the contact side of the dried peeled film is measured before and after decontamination with results showing excellent encapsulation of the contamination. The results are summarized in the following table.

| | Surface - Before Treatment | | Dry Film Surface | | Dry Film - Contact Side | | Surface - After Treatment | |
|---|---|---|---|---|---|---|---|---|
| Surface Surveyed | Direct Read[1] GM Detector[1] (cpm) | Swipe[2] Gamma Counter[2] (cpm) | Direct Read[1] GM Detector[1] (cpm) | Swipe[2] Gamma Counter[2] (cpm) | Direct Read[1] GM Detector[1] (cpm) | Swipe[2] Gamma Counter[2] (cpm) | Direct Read[1] GM Detector[1] (cpm) | Swipe[2] Gamma Counter[2] (cpm) |
| Sink | 31000 | 8415 | 10000 | 0 | 9800 | 29 | 5600[3] | 76 |
| Counter | 80000 | 2679 | 44000 | 0 | 26000 | 2 | 11000[3] | 0 |
| Bedside Floor | 30000 | 53 | 18000 | 0 | 17800 | 0 | 1700 | 0 |
| Bathroom Floor | 2000 | 124 | 300 | 0 | 770 | 0 | 150 | 5 |

[1]Highest reading in area measured with a Victoreen 190 Geiger Mueller Detector

[2]Determined by swiping a 100 $cm^2$ area followed by direct measurement of the swipe with a Quantum 5003 Gamma

[3]In part due to background contamination in pipes under the sink and counter.

Example 11

A jacketed six-liter reactor equipped with a thermocouple, condenser and stir motor is charged under agitation with 3027 g of distilled water, 2018.4 g of denatured ethanol, 116.0 g of DTPA, 17.4 g of sodium dodecyl sulfate, 110.2 g of 10 N sodium hydroxide, 8.7 g of Byk-028, and 754.0 g of Celvol 523, The resulting aqueous composition is agitated until the salts are dissolved. This is followed by the addition of 900.0 g of Celvol 523, 29.0 g of Byk-345, 29.0 g of Byk 420, and 29.0 g Byk 425. The mixture is heated to 82-85° C., held for 30 minutes, and cooled. 29.0 g of blue food coloring and 1.1 g of 10 N NaOH is added to yield Formulation F. Formulation F has a Brookfield Viscosity of 23,940 cps (3 rpm, spindle 4, 25° C.) and 14,150 cps (30 rpm, spindle 4, 25° C.) and a pH=5.2.

Formulation F was evaluated along with Formulation C in a plutonium finishing plant for decontamination of fissile material processing areas on the same surfaces with similar results with the exception of faster dry times in the strongly ventilated environment.

Example 12

A jacketed six-liter reactor equipped with a thermocouple, condenser and stir motor is charged with 5100 g of distilled water, 60.0 g of DTPA, 60.0 g sodium dodecyl sulfate, 60.0 g of 10 N sodium hydroxide and 9.0 g of Byk-028. The resulting aqueous composition is agitated until the salts are dissolved followed by the addition of 900.0 g of Celvol 523. The mixture is heated to 85° C. and held at 85° C. for 30 minutes, then cooled to yield a Formulation G. Formulation G has a Brookfield Viscosity of 13,210 cps (3 rpm, spindle 4, 25° C.) and 14,030 cps (30 rpm, spindle 4, 25° C.) and a pH of 5.52.

Example 13

To 385.4 g of Formulation G are added 218.3 g distilled water, 3.50 g of Byk-348, 1.75 g of blue food color and 87.5 g of a 14.1wt % pre-gel of Bentone DE (a product of Elementis Specialties identified as hectorite clay). The pre-gel is dispersed in distilled water for 45 minutes at 4000 rpm on a Melton CM-100 disperser equipped with a 1.5 inch Cowels Blade. The mixture is blended to yield Formulation H. Formulation H has a Brookfield Viscosity of 105,960 cps (3 rpm, spindle 4, 25° C.) and 19,020 cps (30 rpm, spindle 4, 25° C.).

Formulation H is tested on a variety of substrates including those commonly found in hospital rooms and hospital bathrooms including floor tile, Formica counter tops, porcelain sinks and toilets, chrome fixtures, sealed grout and unsealed grout. The peelability in each case is very good.

The properties for Formulations A, E, F, G and H are summarized in the following table.

0.50 g of blue food color and 25.0 g of a 14.1wt % pre-gel of Bentone DE (dispersed in distilled water for 45 minutes at 4000 rpm on a Melton CM-100 disperser equipped with 1.5 inch Cowels Blade) to yield Formulation J. Formulation J is sprayed from a Wagner Power Painter Pro 2400 psi airless sprayer to form a coating layer which upon drying becomes a peelable film. The aqueous polymer composition has a Brookfield Viscosity of 10,260 cps (6 rpm, spindle 4, 25° C.) and 6170 cps (60 rpm, spindle 4, 25° C.). The dehydrated film is peeled from kitchen floor tile in a single sheet.

Example 16

A 250 ml container is charged under agitation with 168.5 g of Formulation I, 1.00 g of Byk-348, 1.00 g of Byk-080A, 0.50 g of blue food color, 4.00 g of propylene glycol and 25.00 g of a 14.1wt % pre-gel of Bentone DE (dispersed in distilled water for 45 minutes at 4000 rpm on a Melton CM-100 disperser equipped with a 1.5 inch Cowels Blade) to yield Formulation K. Formulation K is applied to a vertical tile using a Wagner Power Painter Pro 2400 psi airless sprayer and dried to form a peelable film. Formulation K has a Brookfield Viscosity of 9,500 cps (6 rpm, spindle 4, 25° C.) and 5,100 cps (60 rpm, spindle 4, 25° C.). The dehydrated film is peeled from kitchen floor tile in a single sheet.

| | Formulation A | Formulation G | Formulation E | Formulation F | Formulation H |
|---|---|---|---|---|---|
| Solvent | aqueous | aqueous | aqueous | water/ethanol | aqueous |
| Thixotrope | None | None | Byk 420/424 | Byk 420/424 | Bentone DE |
| Low Shear Viscosity (cps) | 5100 | 13,210 | 19,960 | 23,940 | 105,960 |
| High Sear Viscosity (cps) | 5480 | 14,030 | 15,790 | 14,150 | 19,020 |
| Thixotropic Index | 0.93 | 0.94 | 1.26 | 1.69 | 5.57 |
| Vertical film thickness (mils)-wet | <3.1 | 3.0-6.0 | 5.7-11.4 | 5.7-11.4 | 12.6-25.2 |
| Vertical film thickness (mils)-dry | <0.5 | <0.5-1.0 | 1.0-2.0 | 1.0-2.0 | 1.5-3.0 |

In the foregoing table, the Thixotropic Index=Low Shear Viscosity (3 rpm, spindle 4, 25° C.)/High Shear Viscosity (30 rpm, spindle 4, 25° C.). The Vertical Film Thickness–Wet=the thickness of the wet film remaining on the vertical surface after application of an excess off coating estimated from the dry film thickness and the theoretical solids. The Vertical Film Thickness–Dry=the measured film thickness after dehydration.

Example 14

A jacketed six-liter reactor equipped with a thermocouple, condenser and stir motor is charged with 5100 g of distilled water, 60.0 g of DTPA, 60.0 g of sodium dodecyl sulfate, 60.0 g of 10 N sodium hydroxide, and 9.0 g of Byk-028. The resulting aqueous composition is agitated until the salts are dissolved. This is followed by the addition of 900.0 g of Celvol 508 (a product of Celanese identified as polyvinyl alcohol, MW=50,000 to 85,000, 87-89% hydrolyzed). The mixture is heated to 85° C. and held at 85° C. for 30 minutes, then cooled to yield Formulation I. Formulation I has a Brookfield Viscosity of 787 cps (3 rpm, spindle 4, 25° C.) and 922 cps (30 rpm, spindle 4, 25° C.) with pH=5.25.

Example 15

A 250 ml container is charged under agitation with 172.5 g of Formulation I, 1.00 g of Byk-348, 1.00 g of Byk-080A, Example 17

A one-liter container is charged under agitation with 385.4 g of Formulation D, 218.3 g of deionized water, 3.50 g of Byk-348, 1.75 g of blue food color, 87.5 g of a 14.1wt % pre-gel of Bentone DE (dispersed in distilled water for 45 minutes at 4000 rpm on a Melton CM-100 disperser equipped with a 1.5 inch Cowels Blade) and 0.035 g of Kathon LX to yield Formulation L. Formulation L is applied to a substrate and dried to form a peelable film.

Example 18

A jacketed three-liter reactor equipped with a thermocouple, condenser and stir motor is charged with 1700.0 g of deionized water, 20.0 g of DTPA, 20.0 g of sodium dodecyl sulfate, 10.00 g of Byk-028, and 10.00 g of Byk-080A. The resulting aqueous composition is agitated until the salts are dissolved followed by the addition of 300 g of Celvol 523. The mixture is heated to 85° C., held at 85° C. for 30 minutes, and then cooled. 100 g of sodium hypochlorite are added and the pH is adjusted to 6.8 with acetic acid or 10 N NaOH. The aqueous composition is then added to a three-liter container. Under agitation at 1000-3000 rpm with a Melton CM-100 disperser equipped with a 1.5 inch Cowels Blade are added 10.80 g of BYK-348, followed by the drop-wise addition of 16.2 g of BYK-420 over a period of approximately 10 minutes. The rotation of the Cowels Blade is increased during addition to maintain a vortex. After the addition is complete, the formulation is dispersed for 45 minutes at 3000 rpm followed by the drop-wise addition of 16.2 g of BYK-425. The formulation is then dispersed for 15 minutes at 3000 rpm followed by the addition of 5.40 g of blue food color and 150.0 g of distilled water. The mixture is dispersed for an additional 15 minutes at 3000 rpm to yield Formulation M. Formulation M is applied to a substrate and dried to form a peelable film.

Example 19

A jacketed six-liter reactor equipped with a thermocouple, condenser and stir motor is charged under agitation with 3027 g of deionized water, 2018.4 g of denatured ethanol, 58.0 g of DTPA, 58.0 g of sodium dodecyl sulfate, 110.2 g of 10 N sodium hydroxide, 8.7 g of Byk-028, and 754.0 g of Celvol 325. The resulting aqueous composition is agitated until the salts are dissolved. This is followed by the addition of 900.0 g of Celvol 523, 29.0 g of Byk-345, 29.0 g of Byk 420, and 29.0 g Byk 425. The mixture is heated to 82-85° C., held for 30 minutes, and cooled. 29.0 g of blue food coloring and 116.0 g potassium hypochlorite are added. The pH of the aqueous composition is adjusted to 9.0 with 10 N NaOH to yield Formulation N. Formulation N is applied to a substrate and dried to form a peelable film.

While the invention has been explained in relation to various embodiments, it is to be understood that various modifications thereof may become more apparent to those skilled in the art upon reading this specification. Therefore, it is to be understood that the invention includes all such modifications that may fall within the scope of the appended claims.

The invention claimed is:

1. A composition for removing a contaminate material comprising metal ions and/or charged particles from a substrate, the composition comprising: water; at least one water-soluble film forming polymer comprising polyvinyl alcohol with a molecular weight in the range from about 13,000 to about 250,000 g/mole and a hydrolysis level in the range from about 75% to about 100%, at least one chelating agent that contains two or more electron donor atoms for forming coordinate bonds to the metal ions and/or charged particles; sodium dodecylsulfonate; and an effective amount of at least one thixotropic additive to allow the aqueous composition to flow when under stress and to resist flow when not under stress; the aqueous composition being capable of forming a wet film on a non-horizontal substrate that upon dehydrating forms a peelable or strippable film;

wherein the chelating agent comprises ethylenediaminetetraacetic acid, diethylenetriaminepentaacetic acid, citric acid, amino acid, aminopolycarboxylic acid, organophosphonate, bisphosphonate, inorganic polyphosphate, salts of any of the foregoing chelating agents, or a mixture of two or more of the foregoing chelating agents and/or salts of the foregoing chelating agents; and wherein the at least one thixotropic additive comprises a thixotropic polymer, pseudoplastic polymer, polyurethane, polyhydroxycarboxylic acid amide, modified urea, urea modified polyurethane, hectorite clay, or a mixture of two or more thereof; and two or more leveling agents selected from polysiloxane, dimethylpolysiloxane, polyether modified dimethylpolysiloxane, polyester modified dimethylpolysiloxane, polymethylalkysiloxane, aralkyl modified polymethylalkylsiloxane, alcohol alkoxylate, polyacrylate, polymeric fluorosurfactant and fluoro modified polyacrylate.

2. The composition of claim 1 wherein the composition further comprises one or more pseudoplastic additives, rheology modifiers, anti-settling agents, defoamers, pigments, dyes, organic solvents, plasticizers, viscosity stabilizers, biocides, viricides, fungicides, chemical warfare agent neutralizers, crosslinkers, humectants, neutron absorbers, surfactants, or a mixture of two or more thereof.

3. The composition of claim 1 wherein the composition has Brookfield Viscosity in the range from about 100 to about 50,000 centipoise at 25° C.

4. The composition of claim 1 wherein the composition has a concentration of water in the range from about 30% to about 97% by weight.

5. The composition of claim 1 wherein the aqueous composition is in the form of a film with a thickness in the range from about 0.25 to about 50 mils.

* * * * *